United States Patent [19]

Umemura et al.

[11] 4,205,010

[45] May 27, 1980

[54] METHOD FOR THE CATALYTICAL PRODUCTION OF ACRYLONITRILE

[75] Inventors: Sumio Umemura; Kyoji Ohdan; Taizo Uda; Tokuo Matsuzaki; Mikio Hidaka; Yasuo Nakamura; Masao Tsuruoka, all of Ube, Japan

[73] Assignee: Ube Industries, Ltd., Ube, Japan

[21] Appl. No.: 718,513

[22] Filed: Aug. 30, 1976

[30] Foreign Application Priority Data

Sep. 5, 1975 [JP] Japan .................... 50/107085

[51] Int. Cl.$^2$ .................... C07C 120/14
[52] U.S. Cl. .................... 260/465.3; 252/437; 252/456; 252/464; 252/467; 252/470
[58] Field of Search .................... 260/465.3

[56] References Cited

U.S. PATENT DOCUMENTS

| | | | |
|---|---|---|---|
| 3,135,783 | 6/1964 | Sennewald et al. | 260/465.3 |
| 3,226,422 | 12/1965 | Sennewald et al. | 260/465.3 |
| 3,642,930 | 2/1972 | Grasselli et al. | 260/465.3 X |
| 3,712,912 | 1/1973 | Hausweiler et al. | 260/465.3 |
| 3,766,092 | 10/1973 | Honda et al. | 260/465.3 X |
| 3,907,859 | 9/1975 | Grasselli et al. | 260/465.3 |

*Primary Examiner*—Joseph Paul Brust
*Attorney, Agent, or Firm*—Miller & Prestia

[57] ABSTRACT

Acrylonitrile can be catalytically produced with a high yield by bringing, at an elevated temperature, preferably of 300° to 470° C., a reaction feed containing propylene, ammonia and molecular oxygen into contact with a catalyst consisting of an oxide composition of the empirical formula: $Mo_aCo_bFe_cX_dO_e$ wherein X denotes at least one atom of an element selected from phosphorus, arsenic, antimony and bismuth and wherein the ratio a:b:c:d:e is in a range of 12:4 to 9:1 to 5:0.01 to 0.07:39.5 to 52.7, said catalyst being prepared by providing an aqueous mixture containing molybdenum-, cobalt- and iron-containing compounds and a phosphorus-, arsenic-, antimony- or bismuth-containing compound, converting the aqueous mixture into a dried solid mixture and calcining the solid mixture at a temperature of at least 550° C.

26 Claims, No Drawings

METHOD FOR THE CATALYTICAL PRODUCTION OF ACRYLONITRILE

The present invention relates to a method for the production of acrylonitrile. More particularly, the present invention relates to a method for the production of acrylonitrile by a catalytic reaction of propylene with ammonia and molecular oxygen in gas phase at an elevated temperature.

Various methods are well-known for the production of acrylonitrile by contacting propylene with oxygen and ammonia in gas phase in the presence of a catalyst at an elevated temperature. Various types of catalysts are also provided for the above methods. The conventional types of catalysts consist mostly of oxide compositions which contain combinations of oxides of a plurality of elements. A large number of the conventional catalysts contain bismuth and molybdenum as catalytic ingredient elements. For example, Japanese Patent Application Publication No. 36-5870(1961) discloses a P—Mo—Bi—O type catalyst, Japanese Patent Application Publication No. 38-17967(1963) an Fe—Bi—Mo—P—O type catalyst, Japanese patent application Publication No. 45-35287(1970) a P—Mo—Bi—Fe—Co—Ni—O type catalyst, Japanese patent application Publication No. 49-4209(1974) a Tl—Mo—Fe—Bi—X—P type catalyst in which X represents a magnesium, cobalt or nickel atom, Japanese patent application Laying-open No. 47-17718(1972) an Mo—Bi—Fe—Mg—P—O type catalyst and Japanese patent application Laying-open No. 48-49719(1973) an Mo—Bi—Fe—Co—O type catalyst. However, use of the conventional types of catalysts in the production of acrylonitrile results in the following disadvantages wherein first, the reaction is required to be carried out at a relatively high temperature of about 450° C. or higher; secondly, the reaction feed is required to be kept in contact with the catalyst over a long period of time to complete the reaction; and thirdly, the yield of acrylonitrile per unit time and per unit amount of the catalyst is relatively low. In addition, the conventional types of catalysts have other disadvantages in that the cost of the catalysts is relatively high because the catalysts contain relatively large amounts of bismuth and molybdenum which are expensive. Further, even when the conventional types of catalysts which are deemed as being effective for producing acrylonitrile with a high percentage of selective conversion of propylene into acrylonitrile, are utilized, if said conventional types are used under such a condition that the reaction is performed with a high percentage of reaction of propylene, a large majority of the conventional types of catalysts exhibits a relatively low percentage of selective conversion of propylene into acrylonitrile.

The percentage of selective conversion of propylene into acrylonitrile mentioned above is hereinafter expressed by the term "selectivity percentage of acrylonitrile".

In view of the above-mentioned disadvantages, it is clear that producing acrylonitrile with a high yield of 80% or more by using the conventional types of catalysts is quite difficult.

Under these circumstances, the inventors' aims were to provide a new type of catalyst capable of converting propylene into acrylonitrile at a relatively low reaction temperature, during a relatively short period of reaction time, and with (a) a high yield percentage of about 80% or more of acrylonitrile, (b) a high reaction percentage of propylene, and (c) a high selectivity percentage of acrylonitrile. In addition, it was required that the new type of catalyst be able to satisfy the above-mentioned aims without using bismuth which is very expensive as a catalytic ingredient element. Even if the new type of catalyst did contain bismuth, it was strongly required that the catalyst contain a smaller proportion of bismuth, with respect to molybdenum, than the amount of bismuth contained in any of the other conventional types of catalysts.

An object of the present invention is to provide a method for the catalytical production of acrylonitrile from propylene, ammonia and oxygen, at a relatively low reaction temperature and a relatively high reaction rate.

Another object of the present invention is to provide a method for the catalytical production of acrylonitrile from propylene, ammonia and oxygen, with (a) a high percentage of yield of acrylonitrile, (b) a high percentage of reaction propylene and (c) a high percentage of selectivity of acrylonitrile.

Still another object of the present invention is to provide a method for the catalytical production of acrylonitrile from propylene, ammonia and oxygen in the presence of a catalyst which contains no or very small amounts of bismuth.

Various studies have been carried out by the inventors of the present invention to attain the above-mentioned objects. As a result of their studies, the inventors have discovered that the above objects can be accomplished by employing a new type of catalyst which comprises a base catalytic component consisting of oxides of molybdenum, cobalt and iron, and a small amount of an additional component consisting of at least one member selected from the group consisting of oxides of phosphorus, arsenic, antimony and bismuth, in an atomic ratio of the above-mentioned elements ranging within a specified scope. The present invention has been developed on the basis of the above-described discovery.

That is, the above-mentioned objects can be accomplished by the method of the present invention which comprises bringing a reaction feed containing propylene, ammonia and molecular oxygen in a gas phase into contact with a catalyst consisting of an oxide composition of the empirical formula:

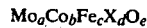

$$Mo_aCo_bFe_cX_dO_e$$

wherein X represents at least one atom of an element selected from the group consisting of phosphorus, arsenic, antimony and bismuth; the subscripts a, b, c and d respectively denote the numbers of the respective atoms of said elements, the ratio a:b:c:d being in the range of 12:4 to 9:1 to 5:0.01 to 0.07; and the subscript e denotes the number of oxygen atoms which satisfies the average valency of the elements, the ratio a:e being in the range of 12:39.5 to 52.7.

The present invention is characterized by using the new type of catalyst mentioned above. This catalyst can exhibit the following technical merits.

(1) Even when used at a temperature of 380° C. or lower which is far lower than the temperature at which the conventional methods of the catalytical conversion of propylene into acrylonitrile are industrially carried out, the catalyst can exhibit a sufficiently high catalytic activity and complete the conversion reaction within a contact period of time of about 2 seconds or less.

(2) Accordingly, the heat necessary to complete the conversion reaction is less than that required in the conventional methods and the catalyst can be used over a period of time longer than that expended in the conventional methods.

(3) Yield of acrylonitrile per unit amount of the catalyst is higher than that in the conventional methods.

(4) Percentages of reaction of propylene and selectivity of acrylonitrile are higher than those in the conventional methods. Accordingly, lesser amounts of by-products from side-reactions and a higher yield of about 80% of acrylonitrile are produced in the present invention than in the conventional methods.

(5) Cost of the new type of catalyst is lower than that of the conventional catalysts, because said new type of catalyst contains no or very small amounts of bismuth.

(6) Accordingly, by using the new type of catalyst, it becomes possible to produce acrylonitrile with a remarkable industrial benefit.

In the new type of catalyst of the present invention, it is necessary that the atomic ratio a:b:c:d is within the range of 12:4 to 9:1 to 5:0.01 to 0.07. If the amounts of the contents of molybdenum, cobalt and iron are outside the above-specified range, the percentage of selectivity of acrylonitrile and the percentage of reaction of propylene decrease. Especially, the percentage of selectivity of acrylonitrile becomes remarkably decreased. If the catalyst contains phosphorus, arsenic, antimony or bismuth in an atomic ratio wherein its upper limit is higher than the above-mentioned upper limit, 0.07, then when the catalytic reaction is performed at a relatively low temperature of about 380° C. or lower in a relatively short contact period of time of about 2 seconds or less, both percentages of selectivity of acrylonitrile and reaction of propylene will decrease. Accordingly, it becomes difficult to produce acrylonitrile with a yield of about 80%. If the atomic ratio of phosphorus, arsenic, antimony or bismuth in the catalyst is lower than the specified lower limit of 0.01, the catalytic activity of the catalyst will be insufficiently small and the yield of acrylonitrile will become undesirably lower.

In the new type of catalyst of the present invention, the elements of the catalytic ingredient exist in the form of oxides thereof. Some of the oxides may form a complex. A plurality of said elements may form a compound together with oxygen.

There are no limitations to the types of preparation methods of the catalyst of the present invention. Generally, the catalyst can be prepared by providing an aqueous mixture containing a molybdenum-containing compound, a cobalt-containing compound, an iron-containing compound and at least one member selected from the group consisting of phosphorus-, arsenic, antimony- and bismuth-containing compounds; converting the aqueous mixture into a dried solid mixture; and calcining the dried solid mixture at a temperature of at least 550° C.

The compounds containing the catalytic ingredient elements may be in the forms of oxides, hydroxides, salts, or acids. The salts are preferably capable of being thermally decomposed. The molybdenum-containing compound may be selected from molybdic acid, ammonium molybdate molybdenum trioxide, phosphomolybdic acid, ammonium phosphomolybdate and molybdenum sulfide.

The cobalt-containing compound may be selected from cobalt carbonate, cobalt nitrate, cobalt (II) oxide, cobalt (III) oxide, cobalt chloride, tricobalt tetroxide, cobalt (II) hydroxide, cobalt (III) hydroxide, and cobalt sulfide.

The iron-containing compound may be selected from ferrous nitrate, ferric nitrate, ferrous oxide, ferric oxide, ferrous chloride, ferric chloride, ferrous hydroxide, ferric hydroxide, ferric phosphate, iron sulfides, ferrous sulfate and ferric sulfate. The phosphorus-containing compound may be selected from pyrophosphoric acid, metaphosphoric acid, phosphoric acid, ammonium phosphomolybdate, phosphomolybdic acid, ammonium phosphate, phosphorus trichloride, diphosphorus tetroxide and diphosphorus pentoxide.

The arsenic-containing compound, may be selected from arsenic chloride, arsenous anhydride, and arsenic pentoxide.

The antimony-containing compound may be selected from antimony trichloride, antimony pentachloride, diantimony trioxide, diantimony pentoxide, antimony oxychloride, antimonous acid, antimonic acid, antimony trisulfide, and antimony pentasulfide.

The bismuth-containing compound may be selected from bismuth chloride, bismuth nitrate bismuth oxide, bismuth oxychloride, bismuth hydroxide and bismuth subnitrate.

In the preparation of the catalyst, the conversion of the aqueous mixture into the solid mixture may be carried out by way of evaporation. Alternately, the aqueous mixture may be subjected to a precipitation treatment by which all of the catalytic ingredient element-containing compounds are precipitated.

The precipitate is separated from the mixture by way of filtering or centrifugalizing and then dried.

The solid mixture thus prepared may be calcined at a temperature of at least 550° C. for a period of time sufficient enough for converting the solid mixture into an activated catalyst. The calcining temperature is preferably in a range from 550° to 700° C. A calcining temperature lower than 550° C., will tend to reduce the percentage of selectivity of acrylonitrile.

A calcining temperature higher than 700° C. will tend to decrease the percentage of reaction of propylene.

The above-mentioned catalyst of the present invention may be composed of the catalytic ingredient alone. However, in order to improve the mechanical strength of the catalyst, it is preferable that the catalytic ingredient be supported on a carrier. The carrier may consist of any type of conventional carrier materials. However, it is preferable that the carrier consists of at least one material selected from the group consisting of silica, alumina, silica-alumina and silicates. There is no limitation to the size and form of the catalyst. That is, the catalyst of the present invention can be screened into a desired size and can be formed into a desired form, for example, powder, grains, granules, pellets or tablets having a desired rigidity, depending upon the purpose and conditions under which the catalyst is to be used. Further, it should be noted that the formation of the catalyst results in no change in the catalytic activity of the catalyst.

For the purpose of illustration, procedures for preparing a catalyst of the present invention consisting of molybdenum, cobalt, iron, phosphorus and oxygen will be described below. A predetermined amount of ammonium molybdate is dissolved in a predetermined amount of water which has been heated to a temperature of 50° to 90° C.

A predetermined amount of phosphoric acid is added dropwise into the above-prepared solution while simultaneously stirring said solution. Further, an aqueous solution containing predetermined amounts of cobalt nitrate and ferric nitrate is added dropwise into the above solution. A slurry mixture is obtained. The slurry mixture is evaporated to form a dried solid mixture. The dried solid mixture is calcined at a temperature of at least 550° C., preferably, from 550° to 700° C. In order to prepare a catalytic composition in which the catalyst is borne on a carrier, it is preferable that the carrier be mixed with the above-mentioned slurry muxture. However, it should be understood that the preparation procedures for the catalyst of the present invention are not limited to the above illustration.

In the method of the present invention, the reaction feed comprises propylene, ammonia and molecular oxygen. This reaction feed can be prepared by mixing a propylene source in gas phase with ammonia and a molecular oxygen-containing gas. The molecular oxygen-containing gas may be an industrially pure oxygen gas. However, it is not required that the molecular oxygen-containing gas have a particularly high concentration of oxygen. Accordingly, the molecular oxygen-containing gas may be air, which is economically advantageous.

The propylene source to be used in the method of the present invention is not required to have propylene of a high purity. However, it is preferable that the propylene source be free from a certain type of compounds, for example, n-butylene and acetylene, which are reactive under the condition wherein propylene is catalytically converted.

In a preferable embodiment of the reaction feed of the present invention, the mole ratio of propylene to oxygen is in a range of 1:1 to 3, more preferably, 1:1.2 to 2, and the mole ratio of propylene to ammonia is in a range of 1:0.5 to 2.0, more preferably, 1:0.8 to 1.2.

The reaction feed can contain an inert diluent gas which does not affect the conversion of propylene into acrylonitrile, for example, nitrogen, carbon dioxide and steam. Especially, steam is effective for increasing not only the selectivity percentage of the aimed acrylonitrile but the durability in catalytic activity of the catalyst. It is preferable that the proportion by mole of the diluent gas to propylene in the reaction feed be 0.5 or more.

The contact of the reaction feed with the catalyst may be effected under ambient pressure, slightly increased pressure or slightly reduced pressure. However, it is convenient that the contact be effected under an ambient pressure.

The reaction in the method of the present invention is carried out at an elevated temperature, preferably, in a range from 300° to 470° C., more preferably, from 330° to 450° C. Particularly, the method of the present invention can be effected at a relatively low temperature in a range from 350° to 400° C., especially, of about 380° C., because the catalyst of the present invention is highly active at the above-mentioned temperature.

There is no limitation with regard to the contact time, of the reaction feed with the catalyst as far as the desired oxidation is completed within said contact time. That is, the reaction of the present invention can be completed by keeping the reaction feed in contact with the catalyst for 0.2 to 10 seconds, preferably, 0.5 to 5 seconds, under an ambient pressure. However, it should be noted that the catalyst of the present invention makes it possible for the reaction to be completed in a contact period of time of between 1 to 3 seconds, particularly, about 2 seconds.

The catalyst of the present invention may be used in a fluidized bed, moving bed or fixed bed. Especially, when the fixed bed is utilized for the method of the present invention, it is preferable that steam be added to the reaction feed, because continuation in the catalytic activity of the catalyst in the fixed bed is increased by the addition of steam.

The resultant acrylonitrile from the method of the present invention may be isolated from the reaction mixture by any conventional isolating method, for example, the methods disclosed in U.S. Pat. Nos. 3,424,781 and 3,688,002.

By applying the method of the present invention, it becomes possible to produce acrylonitrile with a high yield and high selectivity percentage of acrylonitrile while restricting the production of undesirable by-products from side reactions. Further, it should be noted that in the method of the present invention, an increase in the percentage of reaction of propylene does not affect the percentage of selectivity of acrylonitrile. This is one of the industrial benefits provided by the method of the present invention.

The specific examples, shown below will serve to more fully explain the practice of the method of the present invention. However, it should be understood that the examples are only illustrative and should in no way limit the scope of the present invention.

In the examples, the percentage of reaction of propylene, the percentage of selection of acrylonitrile and the percentage of yield of acrylonitrile were respectively calculated in accordance with the following equations:

Reaction percentage of propylene =

$$\frac{X_1 - X_2}{X_1} \times 100,$$

Selectivity percentage of acrylonitrile =

$$\frac{Y}{X_1 - X_2} \times 100,$$

and
Yield percentage of acrylonitrile =

$$\frac{Y}{X_1} \times 100$$

wherein $X_1$ denotes an amout by mole of propylene contained in the reaction feed prior to the start of the reaction, $X_2$ denotes an amount by mole of the residual propylene in the reaction mixture after the completion of reaction, and Y denotes an amount by mole of the resultant acrylonitrile.

EXAMPLES 1 THROUGH 4 AND COMPARISON EXAMPLES 1 AND 2

In Example 1, an aqueous slurry mixture of catalytic ingredients was provided by using the following procedures. First, 170.3 g of ammonium molybdate [$(NH_4)_6.Mo_7O_{24}.4H_2O$] were dissolved in 250 ml of water which had been heated to a temperature of 80° C. while stirring the solution. Next, 0.236 g of phosphoric acid [H₃PO₄] were added dropwise to the above-prepared solution. Thereafter, a second solution which had been prepared by dissolving 187.2 g of cobalt nitrate [CO(NO₃)₂.6H₂O] and 65.0 g of ferric nitrate [Fe(NO₃)₃.9H₂O] in 200 ml of water having a temperature of 80° C., was mixed dropwise with the solution. An aqueous slurry mixture was obtained.

The slurry mixture was heated to a temperature of 120° C. while stirring said mixture so as to form a dried solid mixture of the above-mentioned materials. The dried solid mixture was formed into tablets, each tablet having a diameter of 5 mm and a thickness of 5 mm, said tablets were heated to a temperature of 600° C. at a heating-up rate of 100° C./hr and calcined at the above temperature for 5 hours in a calcining furnace while air flowed therethrough. The resultant catalyst had an atomic ratio of Mo:Co:Fe:P of 12:8:2:0.03.

A reaction column was provided by charging 10 ml of the catalyst prepared above into an U-shaped glass tube having an inner diameter of 8 mm. The reaction column was heated to a temperature of 380° C. and maintained at said temperature. A reaction feed which had been prepared by mixing in gas phase propylene, ammonia, air and steam in a mole ratio of 1.0:1.0:11.0:2.0 was passed through the reaction column at a flow rate of 300 ml/min. The reaction feed was kept in contact with the catalyst for 2.0 seconds.

In Examples 2 and 3, the procedures identical to those in Example 1 were carried out, except that the atomic ratio of Mo, Co, Fe and P in the catalyst was 12:8:2:0.05 in Example 2 and 12:8:2:0.07 in Example 3.

In Example 4, the same procedures as in Example 1 were repeated except that the atomic ratio of Mo, Co, Fe and P in the resultant catalyst was 12:8:2.5:0.03, and the contact of the reaction feed with the catalyst was effected at a temperature of 400° C.

In Comparison Example 1, the same procedures as in Example 1 were repeated, except that no phosphoric acid was used in the production of the catalyst.

In Comparison Example 2, procedures identical to those in Example 1 were repeated, except that the atomic ratio of Mo, Co, Fe and P in the resultant catalyst was 12:8:2:0.5. That is, the proportion of phosphorus in the resultant catalyst was larger than 0.07 which is the upper limit of the proportion of phosphorus in the present invention.

The results of the above-mentioned examples and comparison examples are shown in Table 1.

suspended in the solution while stirring said solution. Thereafter, a second solution which had been prepared by dissolving 186.9 g of cobalt nitrate [Co(NO₃)₆.6H₂O] and 64.9 g of ferric nitrate [Fe(NO₃)₃.9H₂O] in 200 ml of hot water of 80° C., was mixed with the above suspension in order to provide an aqueous slurry mixture.

The slurry mixture suspension was evaporated at a temperature of 120° C. while stirring said suspension to form a dried solid mixture. The solid mixture was formed into tablets, each tablet having a diameter of 5 mm and a thickness of 5 mm. The tablets were heated to a temperature of 600° C. at a heating-up rate of 100° C./hr and calcined at the above temperature for 5 hours to prepare a catalyst. The resultant catalyst had an atomic ratio of Mo:Co:Fe:Sb of 12:8:2:0.04.

The same reaction procedures as in Example 1 were carried out using 10 ml of the above-prepared catalyst. The reaction percentage of propylene was 94.8; the selectivity percentage of acrylonitrile was 84.5; and the yield percentage of acrylonitrile was 80.1.

EXAMPLES 6 THROUGH 9 AND COMPARISON EXAMPLES 3 AND 4

In Example 6, a solution was prepared by dissolving 169.8 g of ammonium molybdate in 250 ml of water which had been heated to a temperature of 80° C. A second solution was prepared by dissolving 1.55 g of bismuth nitrate [Bi(NO₃)₃.5H₂O] in 5 ml of 15% nitric acid. A third solution was provided by dissolving 186.6 g of cobalt nitrate [Co(NO₃)₃.6H₂O] and 64.8 g of ferric nitrate [Fe(NO₃)₃.9H₂O] in 200 ml of hot water having a temperature of 80° C. The second solution and the third solution were added dropwise to the first solution while stirring said solution, in order to provide an aqueous slurry mixture.

The slurry mixture solution was evaporated at a temperature of 120° C. while stirring said solution so as to form a dried solid mixture. The solid mixture was formed into tablets, each tablet having a diameter of 5 mm and a thickness of 5 mm. The tablets were heated to a temperature of 600° C. at a heating-up rate of 100° C./hr and calcined at the above temperature for 5 hours to produce a catalyst. The atomic ratio of Mo:Co:Fe:Bi in the resultant catalyst was 12:8:2:0.04. The same reaction procedures as in Example 1 were effected using 10 ml of the above-prepared catalyst.

In Example 7, procedures identical to those in Example 6 were performed except that the atomic ratio of Table 1

| Item Example No. | Atomic ratio of the elements in the catalytic ingredient | | | | Contact Period of time (second) | Reaction temperature (°C.) | Reaction percentage of propylene | Selectivity percentage of acrylonitrile | Yield percentage of acrylonitrile |
|---|---|---|---|---|---|---|---|---|---|
| | Mo | Co | Fe | P | | | | | |
| Example | | | | | | | | | |
| 1 | 12 | 8 | 2 | 0.03 | 2.0 | 380 | 96.6 | 83.1 | 80.3 |
| 2 | 12 | 8 | 2 | 0.05 | 2.0 | 380 | 96.5 | 85.5 | 82.5 |
| 3 | 12 | 8 | 2 | 0.07 | 2.0 | 380 | 93.0 | 86.0 | 80.0 |
| 4 | 12 | 8 | 2.5 | 0.03 | 2.0 | 400 | 97.4 | 84.7 | 82.5 |
| Comparison Example | | | | | | | | | |
| 1 | 12 | 8 | 2 | — | 2.0 | 380 | 90.4 | 80.3 | 72.6 |
| 2 | 12 | 8 | 2 | 0.5 | 2.0 | 380 | 85.1 | 80.9 | 68.8 |

EXAMPLE 5

First, 250 ml of water were heated to a temperature of 80° C., and 170.1 g of ammonium molybdate [(NH₄)₆.Mo₇O₂₄.4H₂O] were dissolved in the heated water. Next, 0.468 g of antimony trioxide (Sb₂O₃) were Mo, Co, Fe and Bi in the catalyst was 12:8:2:0.07.

In Example 8, procedures identical to those in Example 6 were carried out except that the catalytic reaction was effected at a temperature of 400° C.

In Example 9, the same operations as in Example 6 were repeated except that the calcining temperature for the production of the catalyst was 650° C.

In Comparison Example 3, procedures identical to those of Example 6 were carried out, except that the atomic ratio of Mo, Co, Fe and Bi was 12:8:2:1 in which the proportion of Bi was outside the range of the proportion of Bi in the present invention.

In Comparison Example 4, the same procedures as in Comparison Example 3 were repeated except that the catalytic reaction was effected at a temperature of 400° C.

The results of the above examples and comparison examples are indicated in Table 2.

EXAMPLES 11 AND 12

In Example 11, first an aqueous solution was prepared by dissolving 170.2 g of ammonium molybdate [$(NH_4)_6Mo_7O_{24}.4H_2O$] in 250 ml of water which had been heated to a temperature of 80° C. and, thereafter, dissolving 0.16 g of arsenic trioxide [$As_2O_3$] in the above solution.

A second solution which had been prepared by dissolving 0.78 g of bismuth nitrate [$Bi(NO_3)_3.5H_2O$] in 2.5 ml of 15% nitric acid and a third solution which had been prepared by dissolving 187.0 g of cobalt nitrate [$Co(NO_3)_3.6H_2O$] and 64.9 g of ferric nitrtate [$Fe(NO_3)_3.9H_2O$] in 200 ml of hot water having a tempera- Table 2

| Example No. | | Atomic ratio of the elements in the catalytic ingredient | | | | Calcining temperature (°C.) | Reaction temperature (°C.) | Reaction percentage of propylene | Selectivity percentage of acrylonitrile | Yield of acrylonitrile |
|---|---|---|---|---|---|---|---|---|---|---|
| | | Mo | Co | Fe | Bi | | | | | |
| Example | 6 | 12 | 8 | 2 | 0.04 | 600 | 380 | 96.2 | 83.8 | 80.6 |
| | 7 | 12 | 8 | 2 | 0.07 | 600 | 380 | 96.8 | 82.9 | 80.2 |
| | 8 | 12 | 7 | 2.7 | 0.04 | 600 | 400 | 97.2 | 83.2 | 80.9 |
| | 9 | 12 | 8 | 2 | 0.04 | 650 | 380 | 95.0 | 84.3 | 80.0 |
| Comparison | 3 | 12 | 8 | 2 | 1 | 600 | 380 | 83.1 | 83.5 | 69.5 |
| Example | 4 | 12 | 8 | 2 | 1 | 600 | 400 | 94.8 | 81.0 | 76.8 |

EXAMPLE 10

A solution was prepared by dissolving 170.2 g of ammonium molybdate [$(NH_4)_6Mo_7O_{24}.4H_2O$] in 250 ml of water which had been heated to a temperature of 80° C. and, thereafter, 0.318 g of arsenic trioxide [$As_2O_3$] were dissolved in the above solution. A second solution was prepared by dissolving 187.0 g of cobalt nitrate [$Co(NO_3)_2.6H_2O$] and 64.9 g of ferric nitrate [$Fe(NO_3)_3.9H_2O$] in 200 ml of hot water having a temperature of 80° C. The second solution was added dropwise to the first solution to prepare an aqueous slurry mixture.

The slurry mixture thus prepared was dried at a temperature of 120° C. while stirring said mixture so as to form a solid mixture. The solid mixture was formed into tablets, each tablet having a diameter of 5 mm and a thickness of 5 mm. The tablets were heated to a temperature of 600° C. at a heat-up rate of 100° C./hr and calcined at the above temperature for 5 hours. A catalyst having an atomic ratio of Mo, Co, Fe and As of 12:8:2:0.04, was obtained.

The same catalytic reaction procedures as in Example 1 were carried out using 10 ml of the above-prepared catalyst. In the results of the catalytic reaction, the reaction percentage of propylene was 95.6; the selectivity percentage of acrylonitrile was 82.2; and the yield percentage was 78.6.

ture of 80° C., were added dropwise to the above first aqueous solution while stirring said solution to prepare an aqueous slurry mixture.

The slurry mixture was dried at a temperature of 120° C. while stirring in order to prepare a solid mixture. The solid mixture was shaped into tablets, each tablet having a diameter of 5 mm and a thickness of 5 mm. The tablets were heated to a temperature of 600° C. at a heating-up rate of 100° C./hr and calcined at the above temperature for 5 hours. A catalyst having an atomic ratio of Mo, Co, Fe, Bi and As of 12:8:2:0.02:0.02, was obtained.

Catalytic reaction procedures identical to those in Example 1 were carried out using 10 ml of the above-obtained catalyst.

In Example 12, procedures identical to those mentioned in Example 11 were repeated, except that 0.236 g of phosphoric acid [$H_3PO_4$] were used in place of the arsenic trioxide.

The results of the examples are indicated in Table 3.

Table 3

| Example No. | | Atomic ratio of the elements in the catalytic ingredient | | | | | | Reaction percentage of propylene | Selectivity percentage of acrylonitrile | Yield percentage of acrylonitrile |
|---|---|---|---|---|---|---|---|---|---|---|
| | | Mo | Co | Fe | Bi | As | P | | | |
| Example | 11 | 12 | 8 | 2 | 0.02 | 0.02 | — | 96.8 | 83.9 | 81.2 |
| | 12 | 12 | 8 | 2 | 0.02 | — | 0.03 | 97.0 | 83.5 | 81.0 |

What we claim is:

1. A method for the catalytical production of acrylonitrile, comprising contacting a reaction feed containing propylene, ammonia and molecular oxygen in a gas phase at an elevated temperature with a catalyst consisting of an oxide composition of the empirical formula:

$Mo_aCo_bFe_cX_dO_e$ wherein X represents at least one atom of an element selected from the group consisting of phosphorus, arsenic, antimony and bismuth; the subscripts a, b, c, d and e, respectively denote the numbers of the respective atoms of the element, the ratio a:b:c:d being in the range of 12:4 to 9:1 to 5:0.01 to 0.07; and the subscript e represents the number of oxygen atoms which satisfies the average valency of the elements, the ratio a:e being in the range of 12:39.5 to 52.7.

2. A method as claimed in claim 1, wherein said contact is effected at a temperature of 300° to 470° C.

3. A method as claimed in claim 2, wherein said contact temperature is in a range from 330° to 450° C.

4. A method as claimed in claim 3, wherein said contact temperature is in a range of 350° to 400° C.

5. A method as claimed in claim 4, wherein said contact temperature is approximately 380° C.

6. A method as claimed in claim 1, wherein said contact is carried out for 0.2 to 10 seconds.

7. A method as claimed in claim 6, wherein said contact time period is in a range from 0.5 to 5 seconds.

8. A method as claimed in claim 7, wherein said contact time period is in a range from 1 to 3 seconds.

9. A method as claimed in claim 8, wherein said contact time period is approximately 2 seconds.

10. A method as claimed in claim 1, wherein said reaction feed contains an inert diluent gas.

11. A method as claimed in claim 10, wherein the proportion of the diluent gas to propylene in the reaction feed is 0.5 or more.

12. A method as claimed in claim 10, wherein said diluent gas is selected from steam, nitrogen and carbon dioxide.

13. A method as claimed in claim 1, wherein the source of said molecular oxygen to be present in said reaction feed is either pure oxygen gas or air.

14. A method as claimed in claim 1, wherein the source of said propylene to be present in said reaction feed is free from n-butylene and acetylene.

15. A method as claimed in claim 1, wherein the mole ratio of propylene to oxygen to be present in said reaction feed is in a range of 1:1 to 3.

16. A method as claimed in claim 15, wherein said mole ratio of propylene to oxygen is in a range of 1:1.2 to 2.

17. A method as claimed in claim 1, wherein the mole ratio of propylene to ammonia to be present in said reaction feed is in a range of 1:0.5 to 2.0.

18. A method as claimed in claim 17, wherein said mole ratio of propylene to ammonia is in a range of 1:0.8 to 1.2.

19. A method as claimed in claim 1, wherein said catalyst is borne on a catalytic base selected from silica, alumina, silica-alumina and silicates.

20. A method as claimed in claim 1, wherein said catalyst is either in a fixed bed or in a fluidized bed.

21. A method as claimed in claim 1, wherein said catalyst is prepared by providing an aqueous mixture containing a molybdenum-containing compound, a cobalt-containing compound, an iron-containing compound and at least one member selected from the group consisting of phosphorous-, arsenic-, antimony- and bismuth-containing compounds; converting said aqueous mixture into a dried solid mixture; and calcining said dried solid mixture at a temperature of at least 550° C.

22. A method as claimed in claim 21, wherein said calcining temperature is in a range from 550° to 700° C.

23. A method as claimed in claim 1, wherein said X in the empirical formula is phosphorus.

24. A method as claimed in claim 1, wherein said X in the empirical formula is arsenic.

25. A method as claimed in claim 1, wherein said X in the empirical formula is antimony.

26. A method as claimed in claim 1, wherein said X in the empirical formula is bismuth.

* * * * *